United States Patent
Hughes et al.

(10) Patent No.: US 9,279,748 B1
(45) Date of Patent: Mar. 8, 2016

(54) DISSEMINATED VAPOR CAPTURE DEVICE

(71) Applicant: The United States of America Army Edgewood, Chemical and Biological Center, Washington, DC (US)

(72) Inventors: Thomas M. Hughes, Baltimore, MD (US); Kwok Y Ong, Joppa, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 279 days.

(21) Appl. No.: 14/056,632

(22) Filed: Oct. 17, 2013

Related U.S. Application Data

(60) Provisional application No. 61/793,504, filed on Mar. 15, 2013.

(51) Int. Cl.
  *G01N 1/22* (2006.01)
  *G01N 1/02* (2006.01)

(52) U.S. Cl.
  CPC ........ *G01N 1/2247* (2013.01); *G01N 2001/022* (2013.01)

(58) Field of Classification Search
  CPC ... G01N 1/2247; G01N 2001/22; G01N 1/22; G01N 1/24
  USPC ............... 73/864.51, 863.51, 863.81, 864.73, 73/864.81, 865.5; 436/104
  See application file for complete search history.

(56) References Cited

U.S. PATENT DOCUMENTS

| | | | | |
|---|---|---|---|---|
| 1,753,675 A | * | 4/1930 | Wasson | G01N 7/04 422/88 |
| 3,653,253 A | * | 4/1972 | Olin | G01N 5/00 310/328 |
| 4,484,481 A | * | 11/1984 | Laird | G01N 1/2258 73/863.12 |
| 4,909,090 A | * | 3/1990 | McGown | G01N 1/2214 73/863.12 |
| 6,722,182 B1 | * | 4/2004 | Buettner | B01D 53/30 422/305 |
| 2009/0101172 A1 | * | 4/2009 | Cereceda Balic | B09B 3/0058 134/16 |
| 2011/0058987 A1 | * | 3/2011 | Stocklinger | G01N 30/88 422/119 |

* cited by examiner

*Primary Examiner* — John Fitzgerald
*Assistant Examiner* — David L Singer
(74) *Attorney, Agent, or Firm* — Ulysses John Biffoni

(57) ABSTRACT

A disseminated vapor capture device for challenging a gas sampling apparatus with a vapor stream, includes an inlet being adapted for connection to a vapor generating apparatus producing a vapor stream containing target particles or analytes, an outer shell enclosing an inner chamber in communication with the inlet, the inner chamber being adapted for passing the vapor stream therethrough, an outlet being adapted for connection to a vacuum source, the outlet being in communication with the inner chamber for passing the vapor stream out of the inner chamber, and at least one sampling port in communication with the inner chamber, the at least one sampling port each being configured for coupling engagement with a gas sampling apparatus.

12 Claims, 4 Drawing Sheets

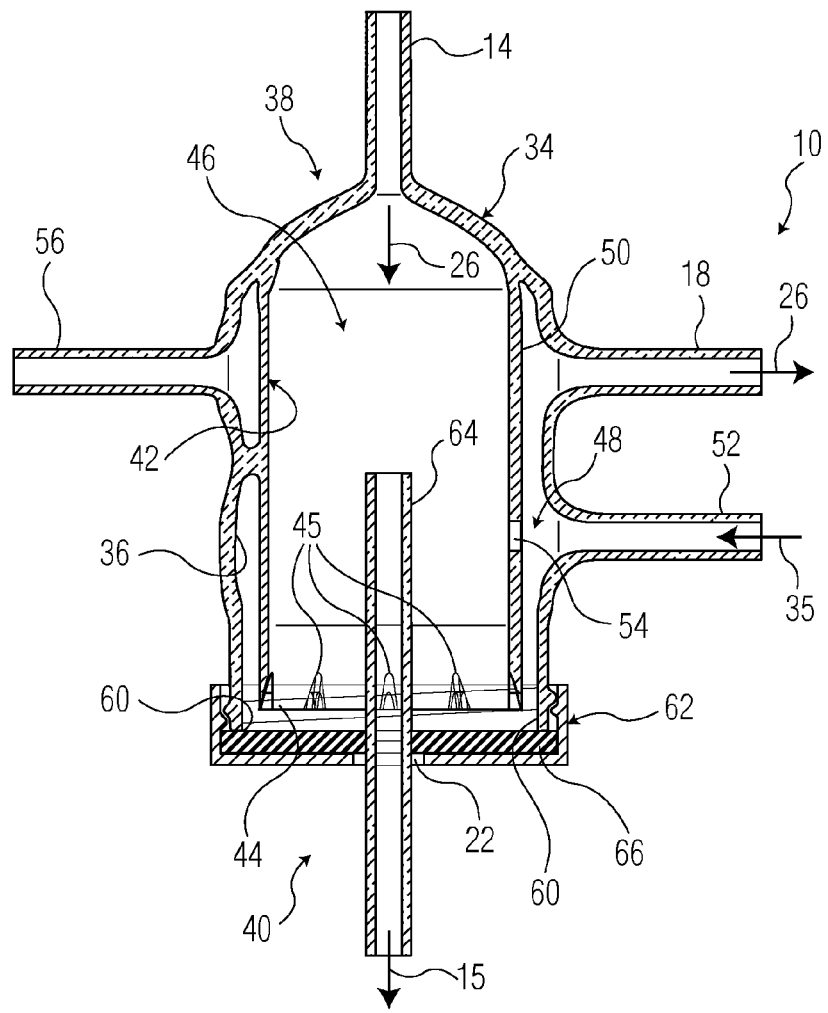
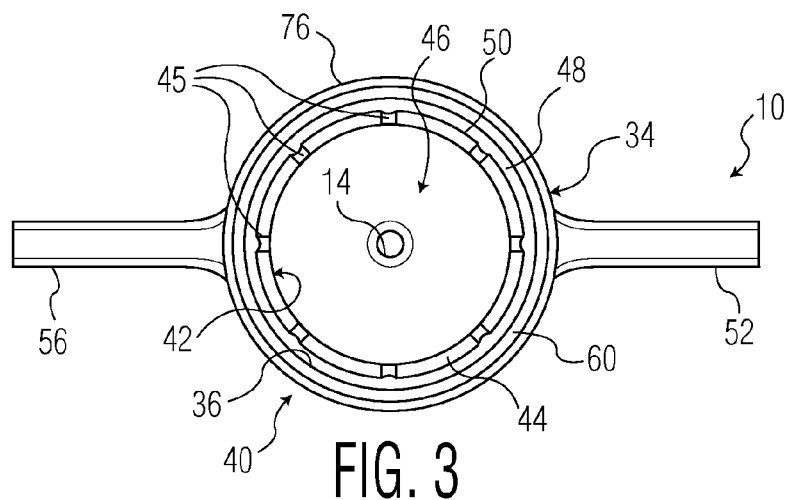

DISSEMINATED VAPOR CAPTURE DEVICE

RELATED APPLICATION

The present Application claims the benefit of priority from U.S. Provisional Patent Application Ser. No. 61/793,504, filed Mar. 15, 2013, the content of which is incorporated herein by reference to the extent it does not conflict herewith.

GOVERNMENT INTEREST

The invention described herein may be manufactured, used and licensed by or for the U.S. Government.

FIELD OF THE INVENTION

The present invention relates to gas dispersing test fixtures, and more particularly to a disseminated vapor capture device configured for disseminating a vapor stream to facilitate testing and evaluating of vapor detection instruments in a safe, reliable and cost effective manner.

BACKGROUND OF THE INVENTION

Chemical weapons used for dispersing chemical warfare (CW) agents over a wide target area pose serious threats to both civilian and military personnel throughout the world. CW agents can be classified into four categories: nerve agents, blister agents, choking agents and blood agents. Some examples of CW agents, which are formulated to inflict death or harm to people, include sarin (GB), soman (GD), distilled mustard (HD), cyanogen chloride (CK), and hydrogen cyanide (AC). In the face of such threats, the ability to rapidly detect and identify CW agents becomes critical to initiating an immediate and effective response to minimize casualties. Such detection relies on the use of vapor detection instruments configured to detect CW agents and other such hazardous vapors. To ensure operational effectiveness, these vapor detection instruments, especially those of newly developed systems, must undergo specific procedures for testing and evaluation prior to service and periodically thereafter.

During testing, test fixtures are typically used to deliver vapor streams containing target particles or analyte to the vapor detection instrument under testing. These test fixtures are generally constructed with an open cup design through which the vapor stream is passed. The open cup includes a closed end through which an inlet is connected to a vapor generating apparatus, and an open end located opposite from the closed end. The gas sampling inlet of the vapor detection instrument is positioned in the test fixture's cup through the open end prior to activating the vapor generating apparatus. Once the vapor generating apparatus is activated, the vapor detection instrument is challenged via the test fixture as the vapor stream disseminates into the open cup from the inlet. Samples of the vapor stream can be collected by the vapor detection instrument through the corresponding gas sampling inlet to provide the necessary test readings.

The open cup design of the test fixtures offers a suitable means for delivering a vapor stream challenge to vapor detection instruments. However, this design provides no safeguard against inadvertent release of potentially dangerous target particles or analytes into the atmosphere at large and contamination of the environment or individuals testing the vapor detection instrument. Because portions of the vapor stream not sampled by a typical vapor detection instrument are expelled through the open end of the cup portion of the associated test fixture, the testing must be carried out under a fume hood to capture the expelled vapors, and minimize its release into the testing work area.

The above arrangement provides sufficient safety for non-toxic or slightly toxic target particles or analytes. However, this arrangement is especially impractical where the target particles or analytes are extremely toxic and too dangerous to handle directly. The operation of the test fixtures in fume hoods can pose undue safety hazards to the testing worker. In such circumstances, the test must be performed with the entire assembly (i.e., vapor generating equipment, reference detector, and vapor detection instrument) inside a glovebox under a fume hood. There are several disadvantages associated with above-mentioned test fixtures and their reliance on fume hoods and/or gloveboxes.

Fume hoods alone provide only limited protection against exposure. In addition to their limited protection, the relatively large size and complexity of such equipment necessitates costly and labor intensive cleanup after multiple testing. With regard to gloveboxes, they are quite expensive to fabricate and use. Although gloveboxes are vastly safer and more effective in isolating the toxic target particles or analytes from the immediate work area, the thick gloves and placement of all the equipment therein, make the testing process more difficult to carry out. Furthermore, the placement of the test equipment including the vapor generating equipment and the vapor detection instrument within the glovebox means that they are exposed to the dangerous chemicals during testing. This necessitates not only cleanup and decontamination of the glovebox interior, but also all the equipment housed therein. Accordingly, extensive labor and cost expenditures are accrued after each use.

Accordingly, there is a need to develop a disseminated vapor capture device configured for challenging a gas sampling apparatus, such as a vapor detection instrument, with a vapor stream containing target particles or analytes in a safe, reliable and cost effective manner. There is a further need for a disseminated vapor capture device capable of disseminating a vapor stream that significantly reduces the risks of a testing worker's exposure to the vapor stream, while offering enhanced portability and convenient operation. There is a further need for a disseminated vapor capture device that is lightweight, compact and relatively inexpensive.

SUMMARY OF THE INVENTION

The present invention relates generally to a disseminated vapor capture device configured for challenging a gas sampling apparatus (e.g., vapor detection instrument) with a vapor stream in a manner that minimizes release of the vapor stream into the ambient atmosphere. The device of the present invention is designed to facilitate chemical vapor detection testing of the gas sampling apparatus to detect target particles or analytes entrained in the vapor stream. The device of the present invention is configured to provide compact containment of the vapor stream with the flexibility of permitting one or more gas sampling apparatuses to be tested for greater efficiency and convenience. The device of the present invention eliminates the need to rely on expensive, bulky and difficult to use fume hoods and gloveboxes that would require subsequent decontamination cleaning of the fume hoods/gloveboxes and the test gear/equipment. The present invention provides a safe, reliable and cost effective means for implementing the testing of gas sampling apparatuses.

In particular, the compact structural features of the present invention enable capture of all excess vapor stream for enhanced safety to testing workers. The device of the present invention is compatible for testing of any gas sampling apparatus regardless of its size, shape or configuration. In addition, the device of the present invention avoids the problem of gross contamination of the gas sampling apparatus under testing that would otherwise occur using prior art methods with gloveboxes, for example, where the entire gas sampling apparatus would be exposed to the vapor stream.

The present device also avoids the need to view the gas sampling apparatus in an enclosed containment and operating it through thick gloves as encountered with the use of the gloveboxes during testing. Any manipulation of the gas sampling apparatus under test, including pressing buttons or reading display screens requires much less effort with this device because a large portion of the apparatus is not enclosed. Further, the present device is relatively inexpensive and simple to make, as compared to the gloveboxes which require significant design, build and installation time, with costs that can reach tens of thousands of dollars.

Accordingly, the device of the present invention is designed to substantially enhance the efficiency and effective dissemination of the vapor stream through its self-contained, compact and lightweight construction, while avoiding or at least substantially minimizing the limitations and problems associated with prior art test fixture devices. The design of the present device also greatly reduces the amount of material required to generate the vapor stream and the target particles or analytes resulting in less waste and further cost savings. Optionally, the device of the present invention can further be configured to permit simultaneous testing of multiple gas sampling apparatuses (e.g., vapor detection instruments) for enhanced savings in time and labor. The device of the present invention is cost effective and relatively simple to make and implement.

In one aspect of the present invention, there is provided a disseminated vapor capture device for challenging a gas sampling apparatus with a vapor stream, in which the device includes:

an inlet being adapted for connection to a vapor generating apparatus producing a vapor stream containing target particles or analytes;

an outer shell enclosing an inner chamber in communication with the inlet, the inner chamber being adapted for passing the vapor stream therethrough;

an outlet being adapted for connection to a vacuum source, the outlet being in communication with the inner chamber for passing the vapor stream out of the inner chamber; and at least one sampling port in communication with the inner chamber, the at least one sampling port each being configured for coupling engagement with a gas sampling apparatus.

In another aspect of the present invention, there is provided a disseminated vapor capture device for challenging a gas sampling apparatus with a vapor stream, in which the device includes:

an outer shell having an interior surface and opposed first and second ends;

an inlet located at the first end of the outer shell for attachment to a vapor generating apparatus;

an inner tubular member enclosed within the outer shell with a truncated open end extending from the inlet toward the second end of the outer shell, the tubular member defining an inner chamber in communication with the inlet;

at least one sampling port located at the second end of the outer shell in communication with the inner chamber, the at least one sampling port each being configured for coupling engagement with a gas sampling apparatus;

a cavity defined by the interior surface of the outer shell, extending along an outer portion of the tubular member, the cavity being in communication with the inner chamber through the truncated open end of the tubular member; and an outlet located on the outer shell in communication with the cavity, wherein the pathway of the vapor stream extends from the inlet, through the inner chamber, the truncated open end of the tubular member, and the cavity, to the outlet.

BRIEF DESCRIPTION OF THE DRAWINGS

The following drawings are illustrative of preferred embodiments of the present invention, and are not intended to limit the invention as encompassed by the claims forming part of the application, wherein like items are identified by the same reference designations:

FIG. 2 is a longitudinal cross sectional view of the disseminated vapor capture device along lines 2-2 of FIG. 1 in accordance with the present invention;

FIG. 3 is a bottom plan view of the disseminated vapor capture device with the cap and sealing member removed showing the structural arrangement of the outer shell and inner tubular member in accordance with the present invention;

DETAILED DESCRIPTION OF THE INVENTION

Figure 1:
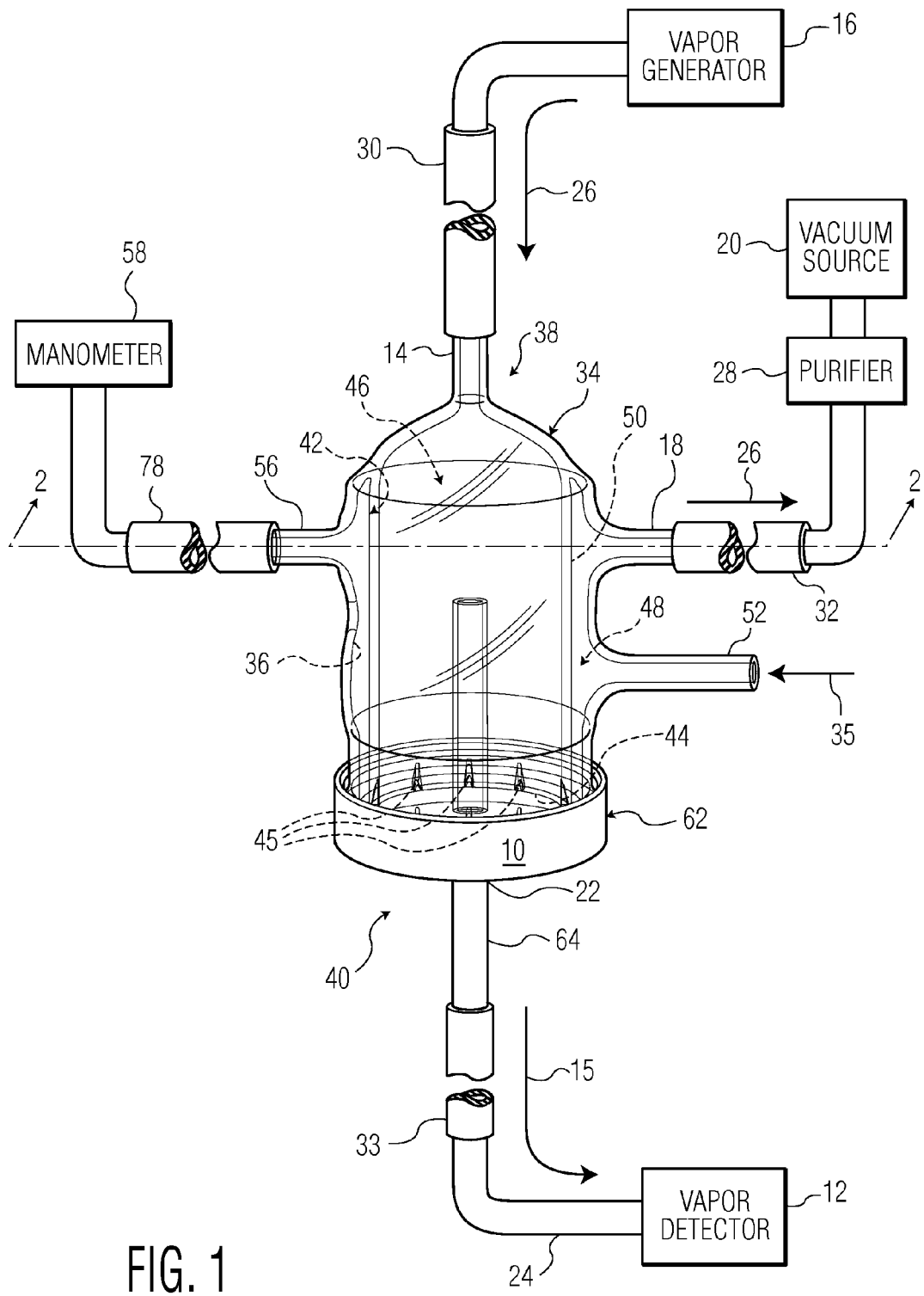
FIG. 1 is a pictorial view of a disseminated vapor capture device prepared for testing a gas sampling apparatus in accordance with one embodiment of the present invention.

The present invention is directed generally to a disseminated vapor capture device configured for challenging a gas sampling apparatus (e.g., vapor detection instrument) with a vapor stream in a manner that minimizes release of the vapor stream into the ambient atmosphere. The device of the present invention is designed to facilitate chemical vapor detection testing of the gas sampling apparatus to detect target particles or analytes entrained in the vapor stream. The device of the present invention is configured to provide compact containment of the vapor stream with the flexibility of permitting one or more gas sampling apparatuses to be tested for greater efficiency and convenience. The device of the present invention eliminates the need to rely on expensive, bulky and difficult to use fume hoods and gloveboxes that would require subsequent decontamination cleaning of the fume hoods/gloveboxes and the test gear/equipment. The present invention provides a safe, reliable and cost effective means for implementing testing of gas sampling apparatuses.

In particular, the compact structural features of the present invention enable capture of all excess vapor stream for enhanced safety to testing workers. The device of the present invention is compatible for testing of any gas sampling apparatus regardless of its size, shape or configuration. In addition, the device of the present invention avoids the problem of gross contamination of the gas sampling apparatus under testing that would otherwise occur using prior art methods with gloveboxes, for example, where the entire gas sampling apparatus would be exposed to the vapor stream.

The present device also avoids the need to view the gas sampling apparatus in an enclosed containment and operating it through thick gloves as encountered with the use of the gloveboxes during testing. Any manipulation of the gas sampling apparatus under test, including pressing buttons or reading display screens requires much less effort with this device because a large portion of the apparatus is not enclosed. Further, the present device is relatively inexpensive and simple to make, as compared to the gloveboxes which require significant design, build and installation time, with costs that can reach tens of thousands of dollars.

Accordingly, the device of the present invention is designed to substantially enhance the efficiency and effective dissemination of the vapor stream through its self-contained, compact and lightweight construction, while avoiding and at least substantially minimizing the limitations and problems associated with prior art test fixture devices. The design of the present device also greatly reduces the amount of material required to generate the vapor stream and the target particles or analytes resulting in less waste and further cost savings. Optionally, the device of the present invention can further be configured to permit simultaneous testing of multiple gas sampling apparatuses (e.g., vapor detection instruments) for enhanced savings in time and labor. Furthermore, the device of the present invention is cost effective and relatively simple to make and implement.

In one embodiment of the present invention, there is provided a disseminated vapor capture device for challenging a gas sampling apparatus with a vapor stream, in which the device includes an inlet being adapted for connection to a vapor generating apparatus producing a vapor stream containing target particles or analytes, an outer shell enclosing an inner chamber in communication with the inlet, the inner chamber being adapted for passing the vapor stream therethrough, an outlet being adapted for connection to a vacuum source, the outlet being in communication with the inner chamber for passing the vapor stream out of the inner chamber, and at least one sampling port in communication with the inner chamber, the at least one sampling port each being configured for coupling engagement with a gas sampling apparatus.

The term "gas sampling apparatus", as used herein, refers to a chemical vapor detection instrument or system containing sensors that generate a signal in the presence of target particles or analytes which may be in the form of hazardous or dangerous chemical vapors or gases in the air, informing personnel of the presence of such chemical vapors or gases. Such gas sampling apparatuses typically include an external gas sampling inlet through which a sample gas flow is collected from the ambient atmosphere. An example of a gas sampling apparatus is the Smiths Detection GID-3™ Chemical Detector marketed by Smiths Detection of Danbury, Conn.

The term "vapor stream", as used herein, refers to a flowing mixture of air entrained with a vapor emission produced by a vapor generating apparatus to which the present invention is operatively connected. The vapor emission contains target particles or analytes at a target vapor challenge concentration. The vapor stream is presented to a gas sampling apparatus via the present invention to test its detection capability. Such vapor generating apparatuses typically rely on precision micro-dispensing technology such as ink jet technology to precisely eject minute amounts of selected chemical compounds and convert them into target particles or analytes in the form of vapor.

For example, this can be achieved by applying an electrical pulse to a piezoelectric micro-dispenser which causes a drop of fluid to be ejected through a precise orifice and the resulting droplets are exposed to heat thereby converting them into vapor. The amount of target particles or analytes challenged can be readily controlled by the number, frequency or size of the droplets generated or concentration of the target compounds in the droplets.

The term "target articles or analytes", as used herein, refers to vapor, gas or aerosol particles or analytes that are used to test the detection capability of a gas sampling apparatus to a particular chemical vapor or gas. The target particles or analytes may be a CW agent or a suitable chemical simulant.

In another embodiment of the present invention, there is provided a disseminated vapor capture device for challenging a gas sampling apparatus with a vapor stream, in which the device includes an outer shell having an interior surface and opposed first and second ends, an inlet located at the first end of the outer shell for attachment to a vapor generating apparatus, an inner tubular member enclosed within the outer shell with a truncated open end extending from the inlet toward the second end of the outer shell, the tubular member defining an inner chamber in communication with the inlet, at least one sampling port located at the second end of the outer shell in communication with the inner chamber, the at least one sampling port being configured for coupling engagement with a gas sampling apparatus, a cavity defined by the interior surface of the outer shell, extending along an outer portion of the tubular member, the cavity being in communication with the inner chamber through the truncated open end of the tubular member, and an outlet located on the outer shell in communication with the cavity, wherein the pathway of the vapor stream extends from the inlet, through the inner chamber, the truncated open end of the tubular member, and the cavity, to the outlet.

With reference to FIGS. 1 and 2, there is shown a disseminated vapor capture device (referred hereinafter as the "device") identified generally by reference numeral 10 in accordance with one embodiment of the present invention. The device 10 is adapted to disseminate a vapor stream 26 containing target particles or analytes to a gas sampling apparatus 12 (e.g., vapor detection instrument or chemical vapor detector) for testing purposes. In this manner, the device 10 functions to simulate the dispersal of target particles or analytes in the ambient atmosphere under conditions which the gas sampling device 12 would encounter in the field. The device 10 is adapted to simulate such conditions within a closed environment preventing any release of the disseminated vapor stream 26 into the ambient atmosphere. The use of the device 10 effectively eliminates the need for gloveboxes/fume hoods to handle or manage the contaminated vapors for substantial savings in terms of cost and labor, while maintaining an elevated level of safety. Although the present invention is described in the context of challenging the sampling apparatus 12 with gases and vapors, it will be understood that the present invention can readily be used in connection with challenging an aerosol sample apparatus with a vapor stream containing an aerosol-type target particles (solids or liquids), as one skilled in the art will recognize.

In one embodiment of the present invention, the device 10 generally includes an vapor stream inlet 14 configured for operatively coupling to a vapor generating apparatus 16 via line tubing 30, an vapor stream outlet 18 configured for operatively coupling to a vacuum source 20 via line tubing 32, and a sampling port 22 adapted for receiving and retaining a sampling tube 64 connected via a line tubing 33 to an external gas sampling inlet 24 of the gas sampling apparatus 12. The sampling port 22 and sampling tube 64, in combination, provide an interface for the gas sampling apparatus 12 to draw a quantity of a gas sample 15 as needed. The vapor generating apparatus 16 is designed to supply a vapor stream 26 containing target particles or analytes to the device 10 through the line tubing 30 and inlet 14. The vacuum source 20 produces a vacuum or pressure drop in the device 10 to draw the vapor stream 26 through the outlet 18.

The vacuum source 20 may include a gas purification module 28 to decontaminate the vapor stream 26 of any dangerous or hazardous chemicals that may be present. In this manner, the vapor stream 26 can be made safe for subsequent release into the atmosphere. The gas purification module 28 may accomplish the decontamination through any suitable means including, but not limited to, filters, sorbents, activated carbon, catalysts, enzymes, thermal treatment, and the like.

The device 10 includes an outer shell or housing 34 having an interior surface 36 and opposing first and second ends 38 and 40, and an inner tubular member 42 enclosed within the outer shell 34. The inner tubular member 42 affixed to the interior surface 36 at the first end 38 of the outer shell 34, coaxially extends downwardly toward the second end 40 terminating into a truncated open end 44. The tubular member 42 defines an inner chamber 46 that is in communication with the inlet 14 located at the first end 38 of the outer shell 34.

The device 10 further includes a cavity 48 defined between the interior surface 36 of the outer shell 34 and an outer portion 50 of the tubular member 42. The cavity 48 is in communication with the inner chamber 46 at the truncated open end 44 of the tubular member 42. The sampling port 22 located at the second end 40 of the outer shell 34 proximate to the inner chamber 46, is configured to receive and retain the sampling tube 64, which extends into the inner chamber 46 for facilitating sampling of the vapor stream 26 passing therethrough. The outlet 18 in communication with the cavity 48 is connected to the vacuum source 20 to generate a pressure gradient much less than atmospheric pressure. The vapor stream 26 is drawn through the device 10 by way of the inlet 14 into the inner chamber 46.

The vapor stream 26 disseminates within the inner chamber 46 allowing the gas sampling apparatus or vapor detector 12 to sample the vapor stream 26 for the target particles or analytes. The disseminated vapor stream 26 then proceeds through the truncated open end 44 of the outer shell 34 and the cavity 48 and exits through the outlet 18 to the vacuum source 20. During vapor dissemination, the vapor stream 26 remains confined within the device 10 and is removed by the vacuum source 20, with none of the vapor stream 26 being released into the ambient atmosphere.

In a further embodiment of the present invention, the device 10 includes an open vent port 52 located on the outer shell 34 proximate the outlet 18 and an access aperture 54 (as shown best in FIG. 2) located on the tubular member 42. The aperture 54 is aligned axially with the vent port 52. The vent port 52 remains open to ambient atmosphere to allow air 35 to entrain with the vapor stream 26 and prevent buildup of excessive negative pressure in the device 10. It is understood that the pressure within the device 10 should be maintained at a suitable level ensuring continuous air flow from ambient through the vent port 52 to avoid release of the vapor stream 26 into the atmosphere. The access aperture 54 provides the testing worker access to the atmosphere of the inner chamber 46 for accurate sampling and vapor concentration determination using a standardized or laboratory gas sampling apparatus (not shown).

In particular, the access aperture 54 allows the testing worker to safely measure the actual concentration of the target particles or analytes in the vapor stream 26. To measure the actual value, the sampling probe (e.g., sorbent tube or bubbler) of the standard or laboratory gas sampling apparatus is inserted through the vent port 52 and access aperture 54 into the vapor stream 26 passing the inner chamber 46. This actual value as measured by the standardized gas sampling apparatus is used to appropriately evaluate, qualify and validate the gas sampling apparatus 12 being tested. The performance, quality, safety, stability and effectiveness of the tested gas sampling apparatus 12 can be determined accordingly.

A pressure port 56 is disposed on the outer shell 34 in communication with the cavity 48 and is adapted for fluid coupling to a pressure measuring apparatus 58 such as a manometer via a line tubing 78. In one embodiment of the present invention, the pressure port 56 is positioned on the side opposite from the outlet 18 to provide a stable reading. The manometer 58 is used to monitor the pressure within the device 10 to ensure proper operation and to detect any unwanted leakage. The presence of leakage can easily be checked by covering the vent port 52 and comparing the corresponding pressure reading of the manometer 58 with the expected pressure reading. If the pressure, measured with the vent port 52 covered, is greater than the expected pressure, then a suspected leak may be present in the device 10. Corrective measures can thereby be taken accordingly.

In a preferred embodiment of the present invention, the outer shell 34 and inner tubular member 42 is constructed from any suitable inert material compatible with the gas medium and the target particles or analytes of the vapor stream 26 and capable of enduring the physical rigors associated with disseminating a vapor stream 26 within the device 10. Examples of such suitable inert material include, but are not limited to, metals, plastics, ceramics, elastomers, and glass. Preferably, the inert material is glass, and more preferably, borosilicate glass. The device 10 can be constructed using any suitable manufacturing processes as known to those skilled in the art, including, but not limited to, glassforming, 3-dimensional printing, casting (e.g., centrifugal, continuous, die), molding (e.g., injection, compression, extrusion), forming (e.g., forging, rolling, extrusion, pressing), machining (e.g., milling, turning, drilling), and the like.

With reference to FIG. 3, the tubular member 42 is configured radially spaced-apart from the outer shell 34, thus defining the cavity 48 therebetween. The truncated open end 44 of the tubular member 42 optionally includes a plurality of spaced apart slots 45 disposed radially along the periphery thereof to facilitate passage of the vapor stream 26 from the inner chamber 46 to the cavity 48 as will be further described hereinafter. The outer shell 34 further includes an externally-threaded opening 60, an internally-threaded cap 62 (see FIGS. 2 and 4) with the sampling port 22 configured for threaded coupling engagement with the externally-threaded opening 60, and a sealing member or gasket 66 disposed between the opening 60 and the cap 62. The sealing member 66 is configured to retain the sampling tube 64 extending through the sampling port 22 of the cap 62 forming a hermetic seal therearound. The distal end of the sampling tube 64 extends into the inner chamber 46.

One embodiment of the present invention includes the sealing member 66 with a resilient, disk-shaped plate body 68 and a centrally located aperture 70 axially aligned with the sampling port 22. The plate body 68 is preferably constructed from an elastomeric material such as, for example, rubber. The sealing member aperture 70 is suitably dimensioned for receiving and retaining the sampling tube 64 in a snug fit. With the cap 62 threadedly engaged to the opening 60, the sealing member 66 is securely packed between the edge portion of the opening 60 and an inside portion 72 of the cap 62, which urges the body 68 to compress inwardly about the sampling tube 64 thereby forming a tight, hermetic seal therearound.

Referring back to FIG. 2, the tubular member 42 of the device 10 is configured to uniformly disseminate the vapor stream 26 generated and supplied by the vapor generating apparatus 16 within the inner chamber 46 from the inlet 14 to the truncated open end 44 of the tubular member 42. The sampling tube 64 is connected to the gas sampling apparatus 12 with its distal end positioned centrally within the inner chamber 46 to allow the vapor stream 26 to be sampled. At the truncated open end 44 of the tubular member 42, the vapor stream is captured in the cavity 48 and exits through the outlet 18. The vent port 52 remains open to the atmosphere to allow make up air to be pulled in from the ambient atmosphere and avoid a build-up of negative pressure in the device 10. The ambient air entrained into the vapor stream 26 passes through the outlet 18.

Figure 4:
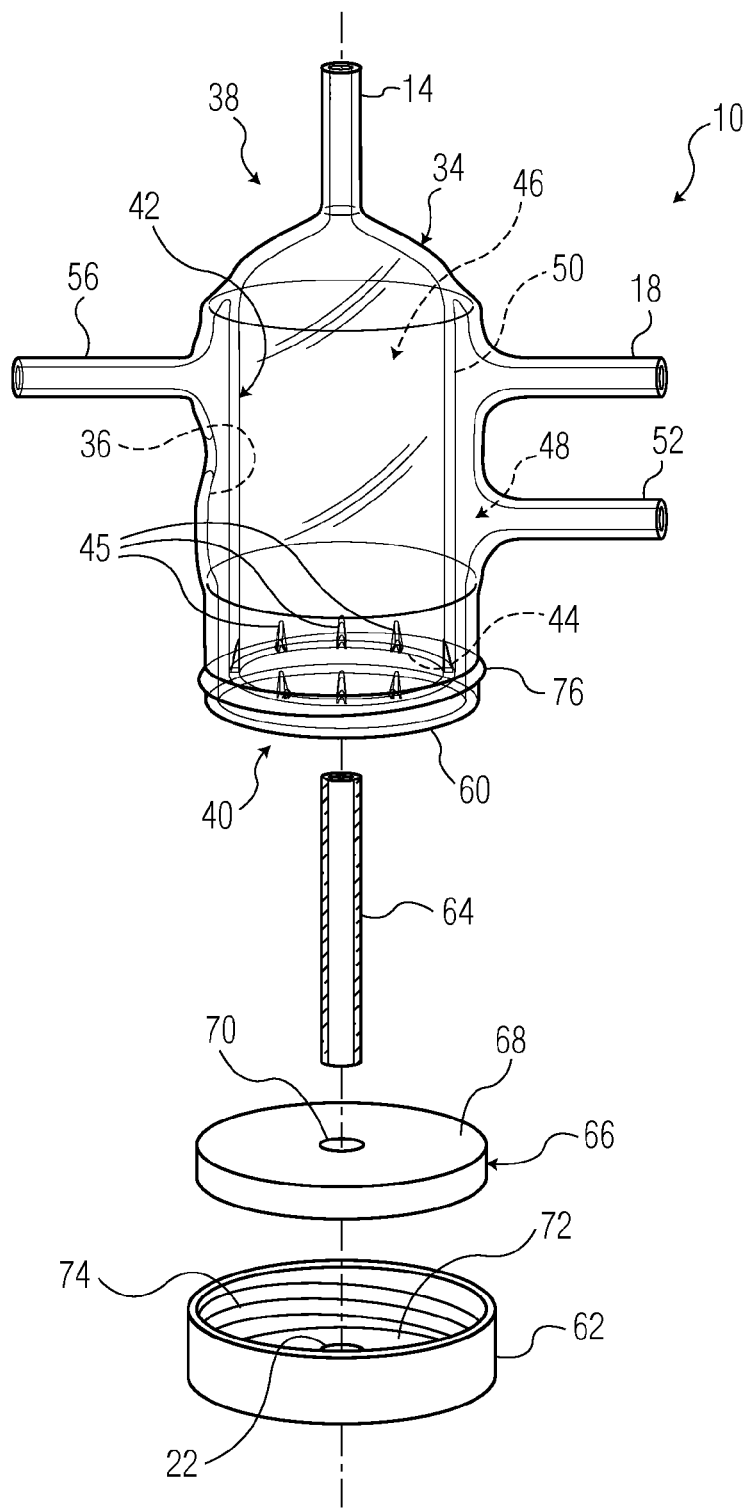
FIG. 4 is an exploded assembly view of the disseminated vapor capture device of FIG. 1 showing all the components thereof in accordance with the present invention.

With reference to FIG. 4, the second end 40 of the outer shell 34 is shown with the cap 62 with internal threads 74 extending along the inside portion 72 thereof, and the opening 60 with external threads 76 extending therearound for threaded mating with the internal threads 74 of the cap 62. The cap 62 includes the centrally located sampling port 22 for receiving and retaining the sampling tube 64 therein. The sealing member 66 is configured for seating within the inside portion 72 of the cap 62 with the aperture 70 disposed therethrough in alignment with the sampling port 22.

Referring back to FIGS. 1 to 4, the overall operation of the device 10 will now be discussed herein. The vapor generating apparatus 16 is connected to the inlet 14 of the device 10 via the line tubing 30. The pressure measuring device 58 is connected to the pressure port 56 of the device 10 via the line tubing 78. The cap 62 is threadedly disengaged from the opening 60 of the outer shell 34, and the sealing member 66 is removed with the cap 62. The sampling tube 64 attached to the external gas sampling inlet 24 of the gas sampling apparatus 12, is inserted through the sampling port of the cap 62 and the aperture 70 of the sealing member 66. The cap 62 and the sealing member 66 are threadedly mounted back onto the threaded opening 60 of the outer shell 34, and secured with the sealing member 66 abutting against the edge portion along the opening 60, while ensuring a hermetic seal about the sampling tube 64.

Once the gas sampling apparatus 12 is secured to the device 10 for testing, verification is made to ensure the entire vapor stream 26 is safely captured. The total air entering the inner chamber 46 is determined for achieving a desired flow rate. Once the flow rate for the device 10 is determined and set through the vapor generating apparatus 16, the vacuum source 20 is connected to the outlet 18 via the line tubing 32. A vapor stream 26 absent the target particles or analytes is passed through the inlet 14 from the vapor generating apparatus 16 at a set flow rate. The vacuum source 20 is set to a flow rate that is higher than the flow rate of the vapor stream 26 passing through the inlet 14. Preferably, the flow rate at the outlet 18 is about 20% higher than the flow rate at the inlet 14.

With the vapor stream 26 flowing, the vent port 52, which is normally open to the ambient atmosphere, is covered. The pressure measuring device 58 should display a negative pressure reading to indicate total capture of the vapor stream 26 (i.e., no leaks). If a positive pressure reading is presented on the pressure measuring device 58, then this indicates that less than all the vapor stream 26 is being captured. Corrective action should be made to avoid release of the vapor stream 26. Once it is verified that the device 10 is operating properly with no leaks, then testing of the gas sampling apparatus 12 can be safely initiated in the usual manner.

Figure 5:
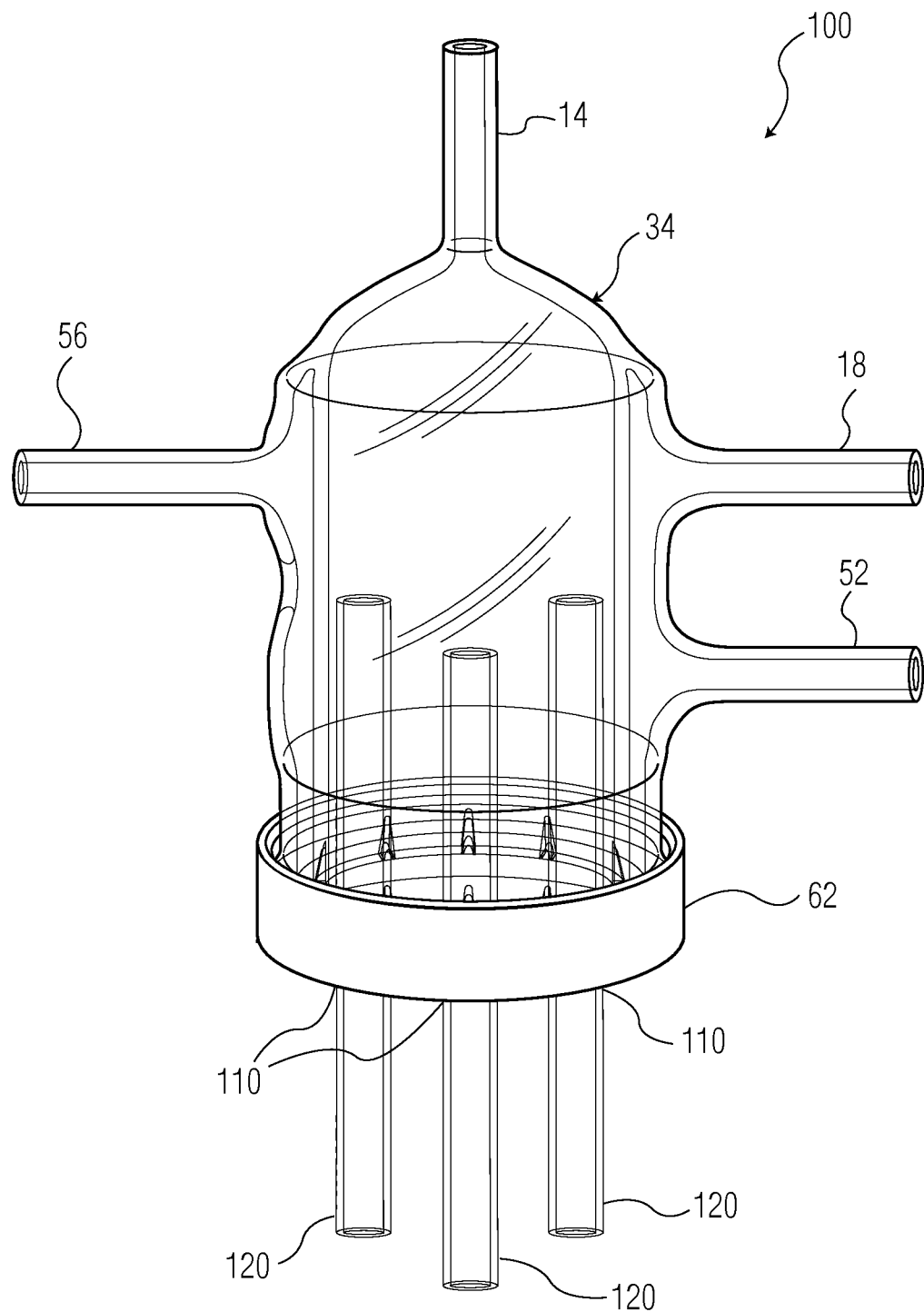
FIG. 5 is a perspective view of the disseminated vapor capture device at a bottom end thereof showing multiple sampling ports in accordance with another embodiment of the present invention.

With reference to FIG. 5, there is shown a disseminated vapor capture device 100 in accordance with another embodiment of the present invention. The structural features of present embodiment of the device 100 are similar to the previous embodiment of the device 10. The device 100 includes a plurality of sampling ports 110 each configured for receiving and retaining a corresponding sampling tube 120 connected to a gas sampling apparatus 12. With this configuration, the device 100 allows the testing worker to test multiple gas sampling apparatuses 12 simultaneously.

EXAMPLE

A prototype of the disseminated vapor capture device 10 was constructed with the following dimensions. It will be understood that the dimensions disclosed herein is not meant to be limiting, and that the following is provided only to illustrate a particular embodiment of the present invention. The outer shell 34 and tubular member device 10 was fabricated from borosilicate glass using conventional glass forming techniques such as, for example, glassblowing.

The inlet 14 of the device 10 connecting the inner chamber 46 to the vapor generating apparatus 16 was formed into a ¼ inch ground glass joint, which allows the vapor stream 26 to be disseminated with the inner chamber 46. The outer shell 34 was about 2 inches in diameter and further included the outlet 18, vent port 52 and pressure port 56, each formed into a ¼ inch ground glass joint. The access aperture 54 was about 3 mm in diameter and formed into the tubular member 42 axially aligned with the vent port 52. The inner chamber 46 had a length of about 2 inches with a diameter of about 1 inch, and the truncated open end 44 was about 1 inch in diameter and spaced about ⅛ inch away from the second end 40 of the outer shell 34. The sampling port 22 of the cap 62 was about ½ inch in diameter.

The sealing member 66 was fabricated from a ⅛ inch thick Viton rubber disk suitably dimensioned to snugly fit with the inside portion 72 of the cap 62. The sealing member aperture 70 was produced through puncturing to snugly receive the sampling tube 64 forming an air tight seal therebetween with the cap 62 threadedly screwed on the opening 60 of the device outer shell 34. The sealing member 66 also formed an air tight seal with the threaded opening 60 of the outer shell 34.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A disseminated vapor capture device for challenging one or more gas sampling apparatus with a vapor stream, said device comprising:
   an outer shell having an interior surface and opposed first and second ends;
   an inlet located at the first end of said outer shell for attachment to a vapor generating apparatus;
   an inner tubular member enclosed within said outer shell, said inner tubular member extending from said inlet toward the second end of said outer shell and having a truncated open end adjacent the second end of said outer shell, said inn tubular member defining an inner chamber in communication with the inlet;
   at least one sampling port located at the second end of the outer shell in communication with the inner chamber, said at least one sampling port each being configured for coupling engagement with one of the one or more gas sampling apparatus;

a cavity defined by the interior surface of the outer shell, extending along an outer portion of the inner tubular member, said cavity being in communication with the inner chamber through the truncated open end of the tubular member;

an outlet located on the outer shell being adapted for connection to a vacuum source, said outlet being in communication with the cavity, wherein a pathway of the vapor stream extends from the inlet, through the inner chamber, the truncated open end of the tubular member, and the cavity, to the outlet;

a vent port located on the outer shell for passing ambient air into the pathway of the vapor stream; and an aperture in the tubular member disposed coaxially with the vent port for permitting sampling access to the inner chamber via the vent port.

2. The disseminated vapor capture device of claim 1, further comprising a pressure port located on the outer shell in communication with the cavity for coupling to a pressure measuring device.

3. The disseminated vapor capture device of claim 2, wherein the pressure port is located on an opposite side from the outlet.

4. The disseminated vapor capture device of claim 1, wherein the outer shell and inner tubular member are composed of an inert material.

5. The disseminated vapor capture device of claim 4, wherein the inert material is selected from the group consisting of metals, plastics, ceramics, elastomers, glass and combinations thereof.

6. The disseminated vapor capture device of claim 5, wherein the glass is borosilicate glass.

7. The disseminated vapor capture device of claim 1, wherein the second end of the outer shell further comprises:
an externally-threaded opening;
an internally-threaded cap configured for threaded coupling engagement with said externally-threaded opening;
said at least one sampling port each having a sampling tube extending through the internally-threaded cap into the inner chamber; and
a sealing member disposed between said externally-threaded opening and said internally-threaded cap for forming a hermetic seal around the sampling tube.

8. The disseminated vapor capture device of claim 7, wherein the sealing member is in the form of a resilient plate.

9. The disseminated vapor capture device of claim 8, wherein the resilient plate is a disk-shaped plate.

10. The disseminated vapor capture device of claim 9 wherein the resilient plate is composed of an elastomeric material.

11. The disseminated vapor capture device of claim 1, further comprising a plurality of spaced apart slots disposed radially along a periphery of said truncated open end of said tubular member.

12. The disseminated vapor capture device of claim 1, wherein the at least one sampling port comprises a plurality of sampling ports each configured for coupling engagement with an individually associated gas sampling apparatus.

\* \* \* \* \*